United States Patent [19]

Quinn et al.

[11] Patent Number: 5,192,691
[45] Date of Patent: Mar. 9, 1993

[54] METHOD FOR SENSING INDIVIDUAL ION CONCENTRATIONS WITHIN MIXTURES USING SAMPLE FRONT ION EXCHANGE ELUTION AND INDIRECT PHOTOMETRIC DETECTION

[75] Inventors: Karen D. Quinn; Theodore E. Miller, Jr., both of Midland, Mich.

[73] Assignee: The Dow Chemical Company, Midland, Mich.

[21] Appl. No.: 845,867

[22] Filed: Mar. 3, 1992

Related U.S. Application Data

[63] Continuation of Ser. No. 319,217, Mar. 3, 1989, abandoned.

[51] Int. Cl.$^5$ ............................................. G01N 30/96
[52] U.S. Cl. ................................. 436/161; 73/61.55; 73/61.56; 422/70; 422/82.05; 436/74; 436/79; 436/178
[58] Field of Search ............... 422/70, 82.05, 82.09; 436/74, 79, 161, 178; 73/61.52, 61.53, 61.55, 61.56, 61.57

[56] References Cited

U.S. PATENT DOCUMENTS

| | | | |
|---|---|---|---|
| 3,926,559 | 12/1975 | Stevens | 422/70 |
| 4,414,842 | 11/1983 | Small et al. | 73/61.1 C |
| 4,674,323 | 6/1987 | Rulf et al. | 422/70 |
| 4,727,034 | 2/1988 | Matsushita et al. | 422/70 |

OTHER PUBLICATIONS

Lederer et al., "Chromatography", ©1957, pp. 3–7, Elsevier Publishing Co.
Chemical Engineers Handbook, Perry & Chilton, pp. 16–45 (Defn. of Frontal Chromatography), ©1973.
Brochure on the DuPont Coumatrak Protime Test System.

*Primary Examiner*—Robert J. Hill, Jr.
*Attorney, Agent, or Firm*—Harness, Dickey & Pierce

[57] ABSTRACT

A method of determining individual ion concentrations in mixtures using ion exchange separation combined with indirect photometric detection and frontal analysis.

8 Claims, 3 Drawing Sheets

METHOD FOR SENSING INDIVIDUAL ION CONCENTRATIONS WITHIN MIXTURES USING SAMPLE FRONT ION EXCHANGE ELUTION AND INDIRECT PHOTOMETRIC DETECTION

This is a continuation of U.S. patent application Ser. No. 319,217, filed Mar. 3, 1989, now abandoned.

BACKGROUND OF THE INVENTION

The present invention relates generally to ion-exchange chromatography and, more particularly, to indirect photometric sensing of optically transparent ion concentrations by frontal analysis.

The determination of which inorganic and/or organic ions are present in solution is a common place and classical analytical problem. One of the most common methods of determining which inorganic and/or organic ions are present in a concentration is by chromatography. The determination of inorganic and/or organic ions which are strong ultraviolet (UV) absorbers in solution has presented few problems to the ion chromatographer. However, the analysis of inorganic and/or organic ions which are weak UV-absorbers or non-UV absorbers in solution has been problematic.

One approach to solving the detection of weak or non-UV absorbers problem is by ion chromatography-eluent suppression. This method is outlined in U.S. Pat. No. 4,474,664, issued to Stevens et al and assigned to the same assignee as the present application, the specification of which is herein expressly incorporated by reference.

Another approach to detect weak or non-UV absorbers is by indirect photometric chromatography (IPC). Briefly, IPC requires the addition of a UV absorbing ion to the mobile phase. A sample plug of unknown ions is injected into the mobile phase. The transparent or non-UV absorbing ions elute through an exchange column and are detected as transients. The detector is coupled with a recorder to provide a chromatogram chart of the results. The addition of the UV absorbing ions to the eluent causes an elevated baseline on the chart. As the non-UV absorbing ions are eluted, negative peaks are produced on the chart corresponding to the qualitative and quantitative information of the sample ions. This method is illustrated by U.S. Pat. No. 4,414,842, issued to Small et al and assigned to the same assignee as the present application, the specification of which is herein expressly incorporated by reference.

Another method of determining ion concentration is by ion selective electrode (ISE) systems. These devices are used especially in clinical environments. ISE systems are among the most widely used chemical systems presently available. Unfortunately, ISE systems are not truly specific but respond more or less to a variety of interfering ions. Other problems associated with the ISE systems are long term drift and accuracy in maintenance requirements. These conditions require that a technically experienced person operates and maintains the apparatus.

While ion chromatography is a reliable method for determining ion concentrations, in its present form, it requires costly equipment and technical expertise to run and maintain this equipment. Thus, a need for inexpensive, simple and reliable methods for ion determination is present in the field.

Thus, there is a desire in the art to move toward portable or miniature apparatus which will enable the determination of ion concentrations away from the laboratory. Also, the procedures should be simple and capable of being interpreted by nontechnical personnel. While the analytical instrumentation should be small, simple and inexpensive, it should also be highly reliable and self-sufficient.

SUMMARY OF THE PRESENT INVENTION

The present invention provides the art with a new method of determining qualitative and quantitative information from sample ion concentrations. The present invention utilizes sample front elution or frontal analysis to determine the information. The present invention provides a readout that is easily interpreted by nontechnical personnel. The readout is composed of individual steps or fronts that qualitatively and quantitatively correspond to the different ions present in the sample. The fronts are analogous to the peaks seen in IPC.

The present invention provides the art with a reproducible method that may be easily conducted outside of the laboratory. The present invention provides a portable unit that may be used to measure sample ion concentrations in situ rather than in the lab.

From the subsequent detailed description taken in conjunction with the subjoined claims and drawings, other objects and advantages of the present invention will become apparent to those skilled in the art.

DETAILED DESCRIPTION OF THE PREFERRED EMBODIMENT

Figure 1:
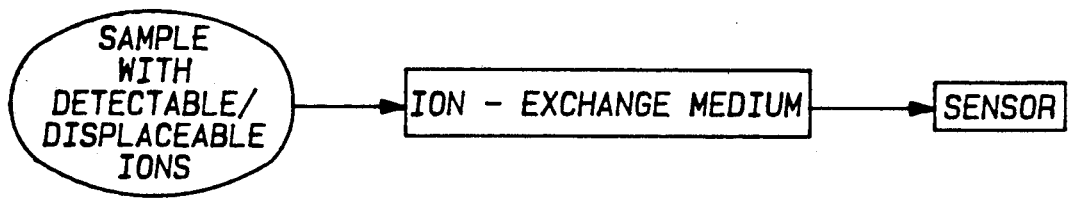
FIG. 1 is a schematic diagram illustrating the present invention.

Referring to the figures, particularly FIG. 1, a sample is combined with a known quantity of detectable/displaceable ions. The sample and known quantity of ions are passed through an ion-exchange medium. The detectable/displaceable ions are sensed by a sensing device to indirectly provide quantitative and qualitative information of the sample ions.

A sample is generally provided which includes unknown photometrically transparent ions. Common photometrically or optically transparent ions are Sodium (Na), Potassium (K), Magnesium (Mg), Calcium (Ca), Chloride (Cl), Sulfate ($SO_4$) or the like. It should be understood that the above list is not exhaustive but only representative of common photometrically transparent ions. These photometrically transparent ions are detected by indirect photometric chromatography by displacing known detectable/displaceable ions in the ion exchange medium to indirectly provide qualitative and quantitative information on the photometrically or optically transparent ions. The sample sizes generally vary from about 0.1 ml to about 100 ml. Samples such as beer, wort, brewing water, softened water, sweat and serum are examples of substances that may be analyzed for ion concentration.

The sample is combined or mixed with a known quantity of detectable/displaceable ions. The detectable/displaceable ions are generally ultraviolet (UV) absorbers but can also be fluorescent. The UV absorbers which perform satisfactorily are generally selected from the group consisting of copper chloride, cerium sulphate octahydrate, chromium chloride, potassium iodide, sodium phthalate and sodium sulfobenzoate. The detectable/displaceable ions may be presented in a liquid solution and mixed with the sample. Also, the detectable/displaceable ions could be a solid or the like and mixed with the sample.

The sample and detectable/displaceable ions form an eluent which is ready to be passed through an ion-exchange medium. The sample is mixed with eluent containing photometric ions in a concentration preferably about equal to or exceeding the combined molar concentrations of the transparent sample ions of interest.

After mixing of the sample eluent, it is passed through an ion-exchange medium via positive or negative pressure. Most media in the art are in the form of pellicular or microparticulate ion-exchange resins. The invention may employ, however, any form of ion-exchange separating medium useful in separating cations or anions by eluting a sample which contains detectable/displaceable ions. Media which work satisfactory are selected from a group consisting of Dowex® 50W-X16 (200-400 mesh), Dowex® 50W-X8 (20-25 micron), (Dowex® is a registered trademark of The Dow Chemical Company), Dowex® may generally be described as a strong cation exchanger, which contains a sulfonic acid bonded to copolymer of styrene and divinyl benzene, Zipax® SCX and SAX (Zipax® is a registered trademark of Dupont) Zipax® SCX may generally be described as a strong cation exchanger, which contains 1% by weight of a sulfonated fluorinated polymer coated on a pellicular silica support; Zipax® SAX may generally be described as a strong anion exchanger, which contains a quaternized polymer coated on a pellicular silica support; and Particil® SCX and SAX (Particil® is a registered trademark of Whatman), Particil® SCX may generally be described as a strong cation exchanger, which contains sulfonic acid bonded to silica through silioxane bonds; Particil® SAX may generally be described as a strong cation exchanger which contains quatenary nitrogen bonded to silica through silioxane bonds. The ion-exchange medium is preloaded until saturated with the detectable/displaceable ions. This enables the ion-exchange medium to react as the eluent is passed through the ion-exchange medium.

Generally, the ion-exchange medium includes a metal, glass or plastic column packed with the ion-exchange resin. The column may be of any desired size and ordinarily will be manufactured in standard sizes. The column sizes range from about 1 mm×2 mm to about 10 mm×250 mm. For a given ion exchange packing and flow rate, large column volume yields better resolution but increases retention time. Smaller column volume allows faster analysis but with decreased resolution.

Figure 2:
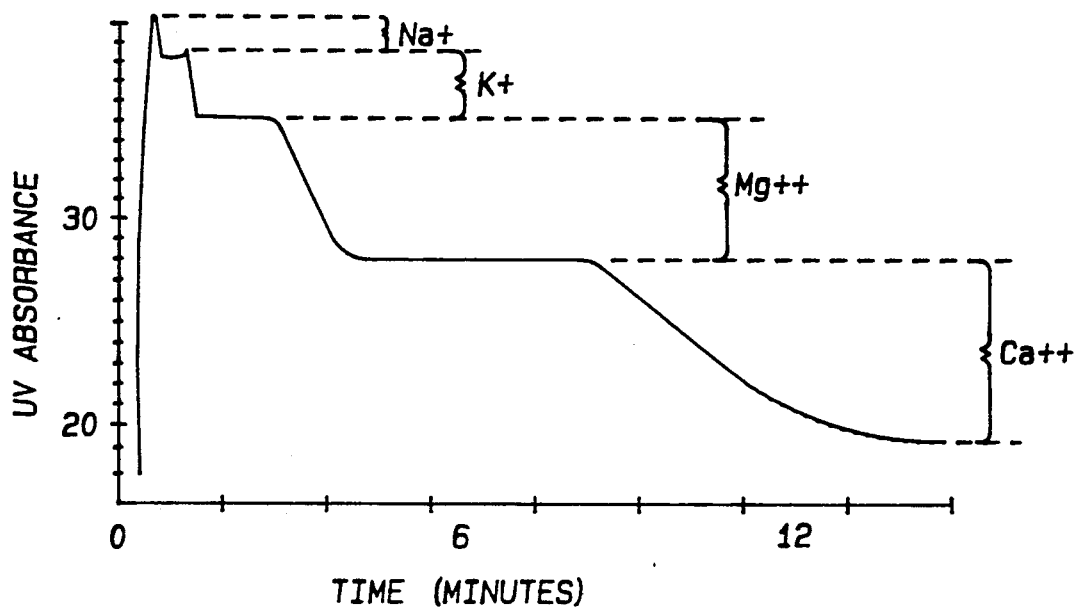
FIG. 2 is a response pattern or output with a calibrated graph illustrating a frontal curve.

As the eluent moves through the ion-exchange medium, it is detected by a sensor or the like. A conventional high performance liquid chromatography UV detector, optical probe or the like may be utilized to sense the detectable/displaceable ions. The detector is coupled with a recorder, such as a Linear Model 166, that produces a curve or chromatogram like that illustrated in FIGS. 2-9. As the fronts pass through the ion-exchange medium and are detected, a plateau or front is recorded on the chart for each particular type of detectable ions present in the sample. In FIG. 2, the fronts illustrate that Na+, K+, Mg++ and Ca++ ions were present in the sample. The absorbance or concentration is measured along the ordinate axis while time is measured along the abscissa.

The heights of the plateaus or fronts correspond to the quantitative molar concentration of the photometrically transparent ions in the sample. The lengths of the plateaus, which correspond to the time it takes the sequential ions to elute, which times are based upon the flow rate, determines the particular qualitative information of the photometrically transparent ions present. It has been found that the photometrically transparent ions will elute at predictable and repeatable positions on the chart during the time period of elution. Thus, one can readily view the plateaus to determine the quantitative and qualitative information concerning the ions present in the sample, as seen in FIG. 2. That is, a nontechnical person may view the plateaus or fronts, compare them to standards for the ions and determine the concentration of the ions and also which ions are present in the sample.

Figure 3:
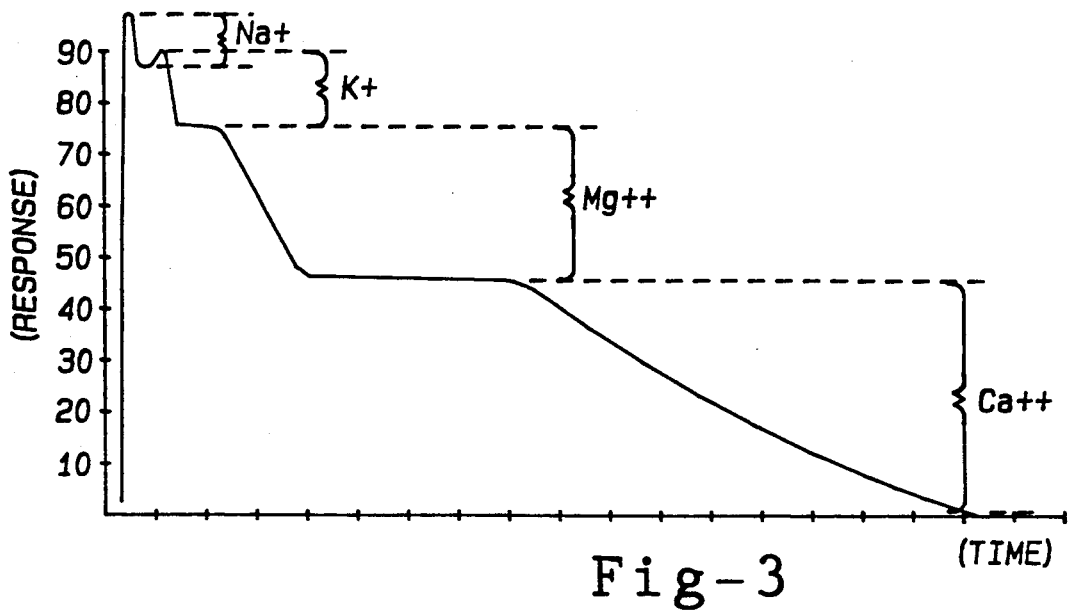
FIGS. 3 through 9 illustrate various types of response patterns or outputs and graphs, as explained herein.
Figure 4:
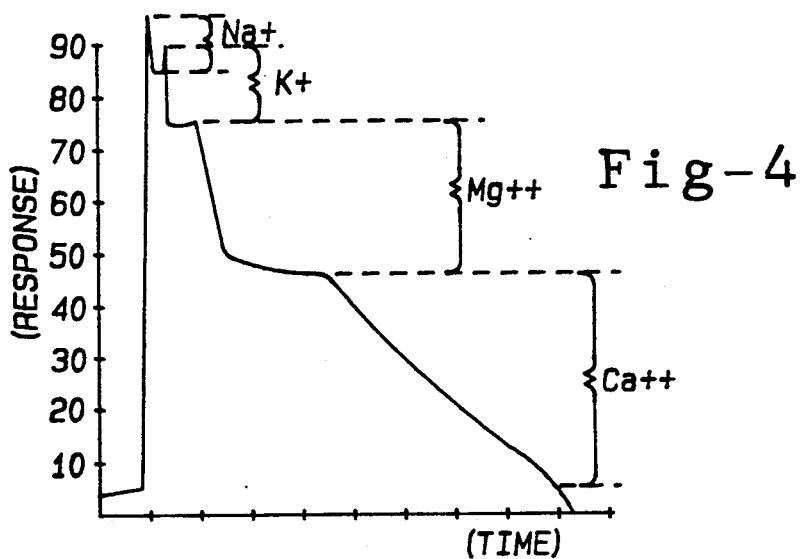
Figure 5:
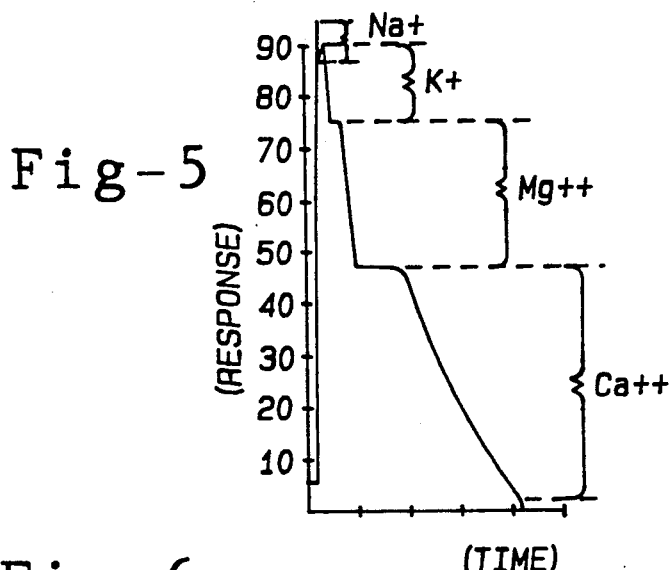

FIGS. 3 through 5 illustrate a response pattern of $1.5 \times 10^{-4}$M solution each of Na+, K+, Mg++ and Ca++ using $10^{-4}$M Ce(III)SO$_4$ as the detectable/displaceable ion, at flow rates of 0.5, 1.0 and 2.0 ml/min, respectively. As can be seen, the plateaus or fronts are at substantially the same vertical position in each of the three figures. The flow rate produces essentially no change in the heights of the individual plateaus or fronts. This is in contrast with conventional chromatography wherein flow rate has a pronounced effect on resolution. The independence of the response from the flow rate is a definite advantage of the present invention and in the development of a disposable ion sensor package.

Figure 6:
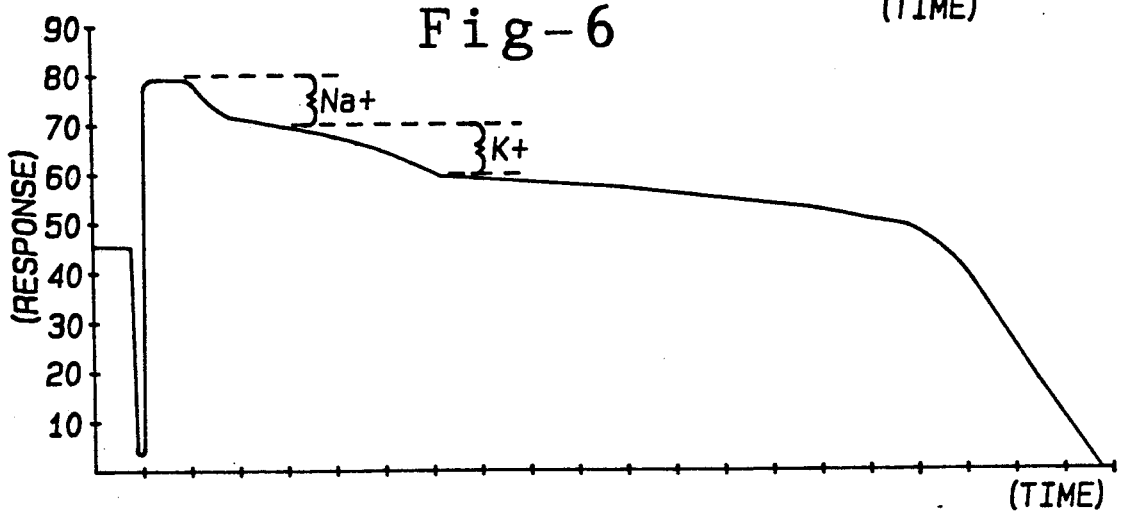
Figure 7:
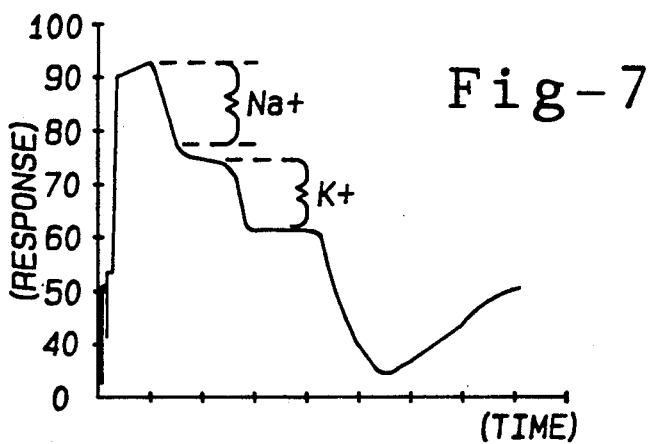
Figure 8:
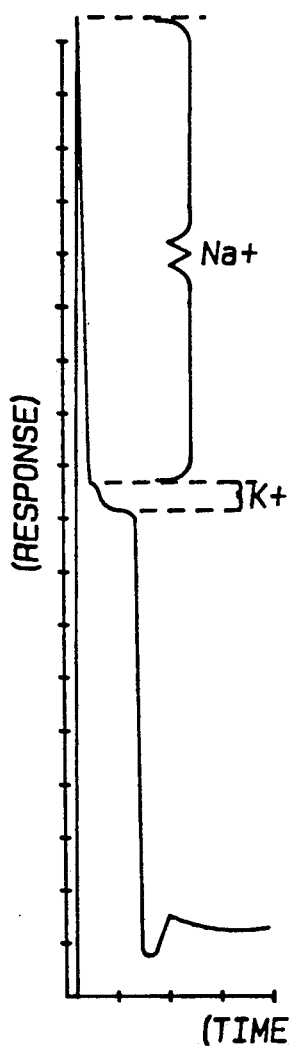
Figure 9:
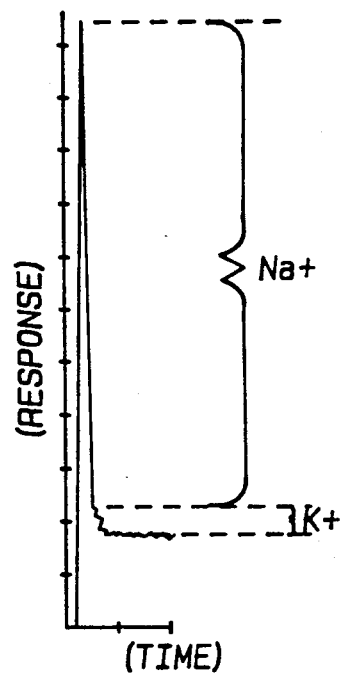
Figure 10:
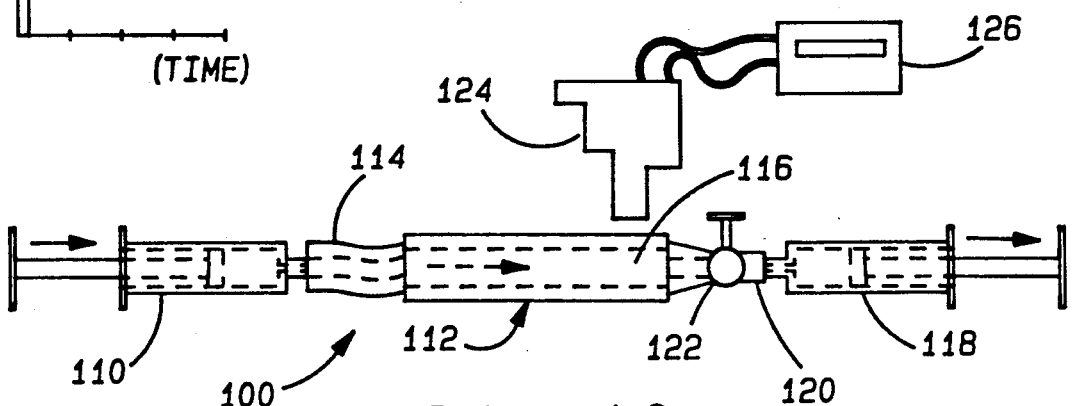
FIG. 10 illustrates an apparatus in accordance with the present invention.

FIGS. 6 through 9 illustrate response patterns of $3 \times 10^{-3}$M each of Na+ and K+ using $10^{-2}$M CuCl$_2$ as the detectable/displaceable ion, at a flow rate of 2.0 ml/min; $6 \times 10^{-3}$M each of Na+ and K+ using $10^{-2}$M CuCl$_2$ at a flow rate of 2.0 ml/min; 0.15M Na+ and $6 \times 10^{-3}$M K+ using $10^{-2}$M CuCl$_2$ at a flow rate of 2 ml/min; 0.15M Na+ and $6.0 \times 10^{-3}$M K+ using $10^{-2}$M CuCl$_2$ at a flow rate of <0.1 ml/min; respectively FIGS. 6 and 7 illustrate that particle size of the ion exchange medium affects the plateau resolution. Smaller particle size in a narrower range result in sharper, more resolved fronts, as seen in FIG. 7. FIGS. 8 and 9 illustrate high concentrations of Na+, which are typical of physiological fluid or water (after softening) samples.

An example of an apparatus 100 used in the present invention comprises a syringe 110 or the like retaining the sample and detector detectable/displaceable ions. The syringe 110 would be connected to an ion-exchange column 112 by an inert connection 114, such as Teflon or the like. The column 112 can be formed from glass or plastic and can be packed with an ion-exchange medium 116 such as Dowex® 50W-X8 resin. A second syringe 118 can be positioned at the other end of the ion-exchange column 112 and connected to the exchange column 112 by an inert conduit 120, such as Teflon or the like. The second or vacuum syringe 118 may have a stop valve 122 between the syringe 118 and the column 112. The syringe 118 barrel can be drawn back to create a vacuum and the stop valve 122 opened to enable the vacuum to draw the solution of the sample and the detectable/displaceable ions from the first syringe 110 through the ion-exchange medium 116. Also, a pump or the first syringe 110 acting as a pump may be used to move the solution through the ion-exchange medium 116. A detector 124 such as a conventional HPLC UV detector with a detector wavelength of $\lambda = 254$ mn and 0.16 AUFS with a strip chart recorder 126 at a speed of 30 cm per hour can be used to record a characteristic frontal pattern of the sample like those illustrated in FIGS. 2 through 9.

While the above detailed description describes the preferred embodiment of the present invention, it will be understood that the present invention is susceptible to modifications, variations and change without deviating from the scope and fair meaning of the subjoined claims.

What is claimed is:

1. An indirect photometric method of sensing photometrically transparent ion concentrations in situ by frontal analysis comprising:
   providing a sample including photometrically transparent ions;
   providing a known quantity of detectable ions;
   combining said sample and said detectable ions to form a solution prior to forcing either of said sample or said detectable ions into an ion exchange medium;
   disposing said solution in a retaining member operable to forcibly urge said solution therefrom upon the application of manual force by an operator thereto;
   passing only said solution including said sample with said photometrically transparent ions and said known quantity of detectable ions through an ion exchange medium; and
   sensing the detectable ions to indirectly provide qualitative and quantitative information on said photometrically transparent ions from descending sample fronts eluting from said ion exchange medium.

2. The method of claim 1 further comprising preloading said ion exchange medium with said detectable ions.

3. The method according to claim 1 further comprising providing a readout of the qualitative and quantitative information.

4. The method according to claim 1 further comprising providing UV absorbing ions as the detectable ions.

5. The method according to claim 1 further comprising said detectable ions selected from the group consisting of copper chloride, cerium sulfate octahydrate, chromium chloride, potassium iodide, sodium phthalate and sodium sulfobenzoate.

6. A method of sensing ion concentrations comprising:
   providing a sample including photometrically transparent ions;
   providing a known quantity of detectable ions;
   combining said sample and detectable ions to form a mixture prior to forcing either of said sample of photometrically transparent ions or said detectable ions into an ion exchange medium;
   disposing said mixture in a retaining member, wherein said retaining member includes means for enabling an operator to manually, forcibly expel said mixture therefrom;
   providing an ion exchange medium in communication with said retaining member having an input end and an output end which is saturated with said detectable ions;
   forcing said mixture including said sample with said photometrically transparent ions and said known quantity of detectable ions from said retaining member into said ion exchange medium through said input end;
   simultaneously generating a negative pressure at said output end to aid in drawing said sample through and out from said ion exchange medium; and
   sensing the detectable ions by frontal analysis to indirectly provide qualitative and quantitative information on said photometrically transparent ions.

7. The method of claim 6 further comprising said detectable ions selected from the group consisting of copper chloride, cerium sulfate octahydrate, potassium iodide, sodium phthalate and sodium sulfobenzoate.

8. The method according to claim 6 further comprising said ion exchange medium selected from the group consisting of a strong cation exchanger, which contains a sulfonic acid bonded to copolymer of styrene and divinyl benzene, a strong cation exchanger, which contains 1% by weight of a sulfonated fluorinated polymer coated on a pellicular silica support, a strong anion exchanger, which contains a quaternized polymer coated on a pellicular silica support, a strong cation exchanger, which contains sulfonic acid bonded to silica through silioxane bonds, and a strong cation exchanger which contains quatenary nitrogen bonded to silica through silioxane bonds.

* * * * *